US00PP37488P2

(12) United States Plant Patent
Philley

(10) Patent No.: US PP37,488 P2
(45) Date of Patent: Jun. 23, 2026

(54) BERMUDAGRASS PLANT NAMED 'MSB-1080'

(50) Latin Name: *Cynodon dactylon*
Varietal Denomination: MSB-1080

(71) Applicant: Mississippi State University, Starkville, MS (US)

(72) Inventor: H. Wayne Philley, Mathisthon, MS (US)

(73) Assignee: Mississippi State University, Starkville, MS (US)

( * ) Notice: Subject to any disclaimer, the term of this patent is extended or adjusted under 35 U.S.C. 154(b) by 0 days.

(21) Appl. No.: 19/228,067

(22) Filed: Jun. 4, 2025

(51) Int. Cl.
*A01H 5/12* (2018.01)
*A01H 6/46* (2018.01)

(52) U.S. Cl.
USPC ..... Plt./389

(58) Field of Classification Search
USPC ..... Plt./389
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new Bermudagrass plant particularly distinguished by having high turfgrass quality and density; medium-fine leaf texture, rapid spring greenup, and low seedhead production.

4 Drawing Sheets

Genus and species: *Cynodon dactylon.*
Variety denomination: 'MSB-1080'.

BACKGROUND OF THE NEW PLANT

Bermudagrass 'MSB-1080' is a new and distinct bermudagrass cultivar. The female parent is 'MSB-1002' (unpatented), the male parent is 'MSB 98' (unpatented). Accordingly, 'MSB-1080' is a tetraploid (2n=4x=36). Cross pollination was performed in summer of 2017 in Starkville, Mississippi and seeds from the cross were germinated in February 2018 in a controlled-temperature chamber. The seedlings were then individually transplanted to a greenhouse. 'MSB-1002' is a progeny of 'MS Choice' (U.S. Plant Pat. No. 10,332; female parent) and Celebration® ('Riley's Super Sport', U.S. Plant Pat. No. 11,181; male parent). 'MSB-1002' was not advanced to any trials and therefore 'MSB-1080' is being compared to its male parent 'MSB 98' and Celebration®. 'MSB-1080' has been vegetatively propagated since germination. 'MSB-1080' was found to reproduce true to type in successive generations of asexual propagation via vegetative cuttings (sod and sprigs) in the greenhouse and in the field in Starkville, Mississippi.

SUMMARY

The following are the most outstanding and distinguishing characteristics of this new variety when grown under normal horticultural practices in Starkville, Mississippi.

1. 'MSB-1080' is characterized by high turfgrass quality and density;
2. 'MSB-1080' is characterized by medium-fine leaf texture,
3. 'MSB-1080' is characterized by rapid spring greenup, and
4. 'MSB-1080' is characterized by low seedhead production.

DESCRIPTION OF THE PHOTOGRAPHS

This new Bermudagrass plant 'MSB-1080' is illustrated by the accompanying photographs. The colors shown are as true as can be reasonably obtained by conventional photographic procedures.

Figure 1:
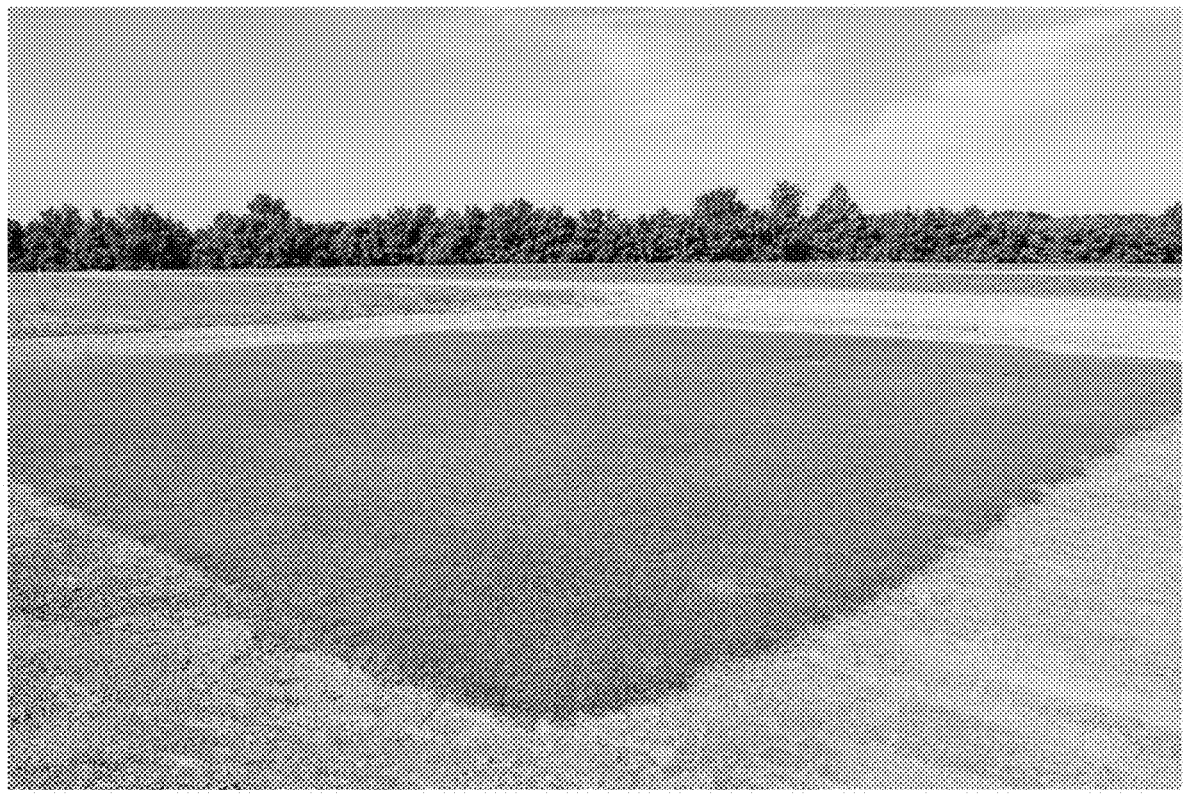

FIG. 1. Photo of 'MSB-1080' plot in Mississippi.

Figure 2:
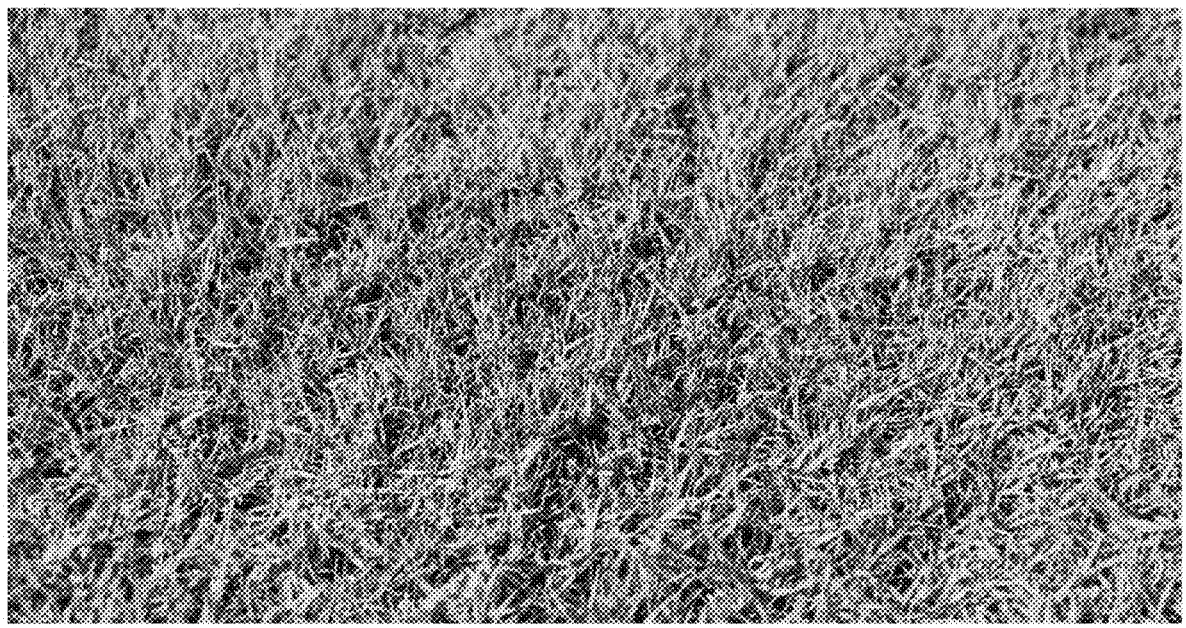

FIG. 2. Close-up photo of leaves of 'MSB-1080' in Mississippi from May 2024.

Figure 3:
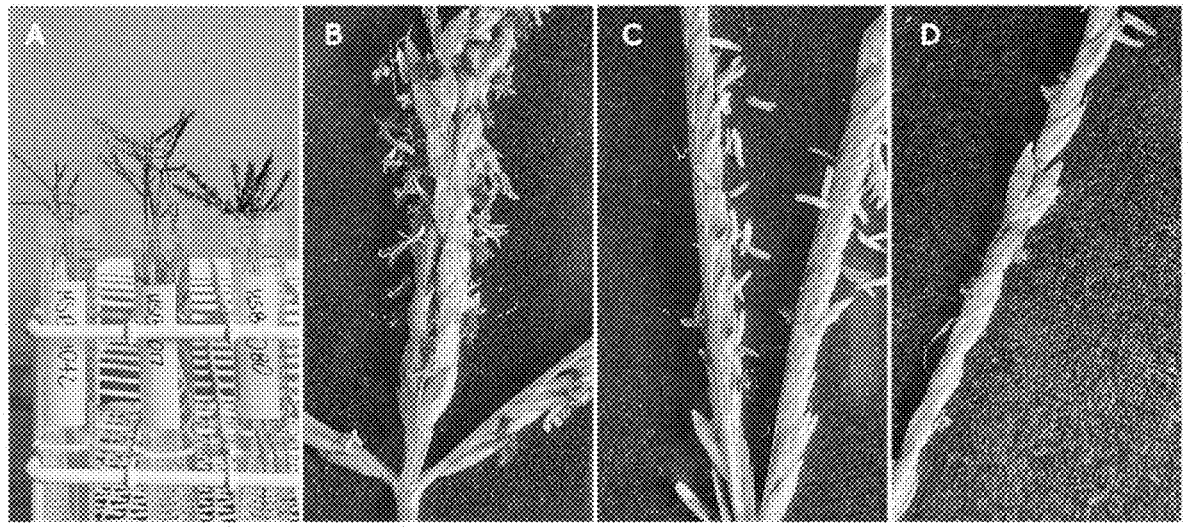

FIG. 3. Photo taken in August 2024 in Mississippi comparing the flowers of 'MSB-1080', 'MSB-1017' and 'MSB-1042'. A—comparison of inflorescences of MSB-1080, MSB-1017 and MSB-1042 side by side. B—close-up pictures of flowers of 'MSB-1080', C—close-up pictures of flowers of 'MSB-1017', D—close-up pictures of flowers of 'MSB-1042'.

Figure 4:
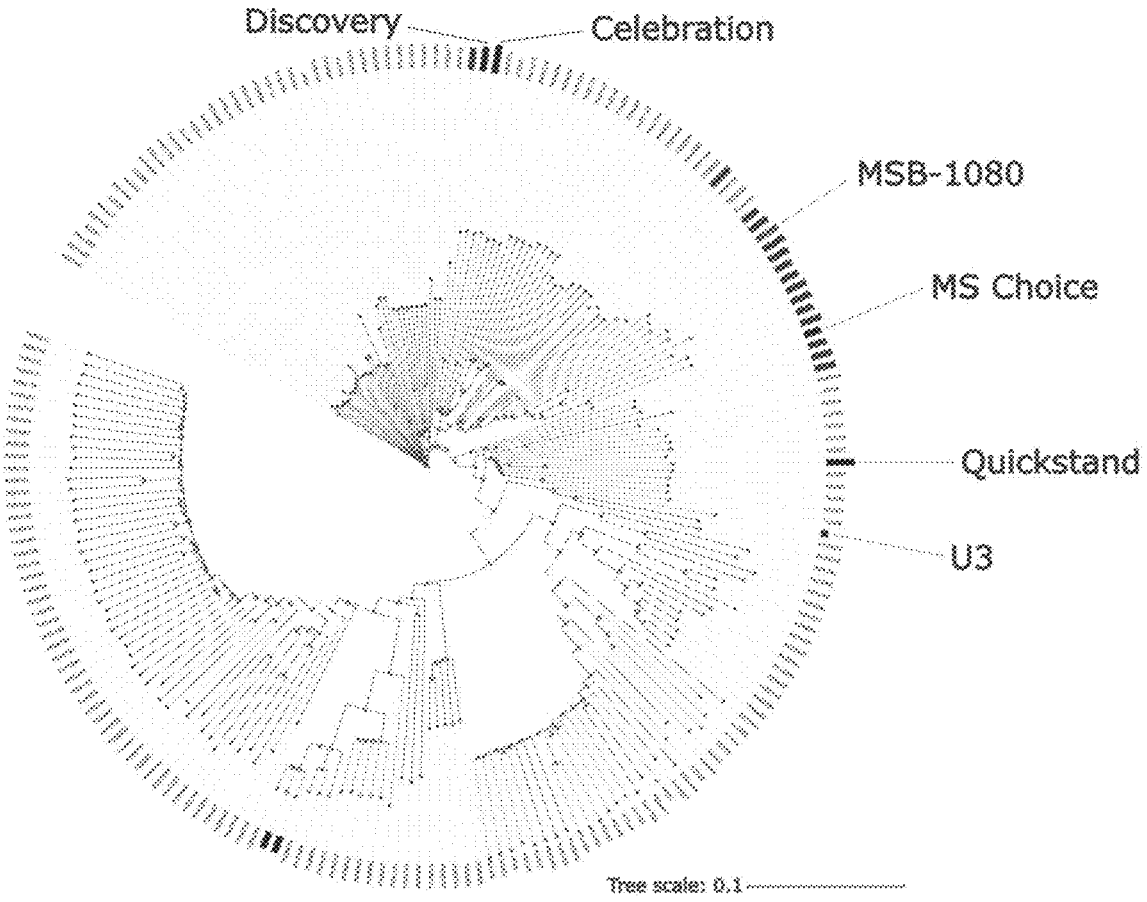

FIG. 4. is a pictorial representation of a phylogenetic tree that shows 'MSB-1080' is genetically different from the other bermudagrass cultivars analyzed.

DESCRIPTION OF THE NEW VARIETY

The following detailed descriptions set forth the distinctive characteristics of 'MSB-1080'.

'MSB-1080' has been evaluated in two trial sites:

Site One: Starkville, Mississippi between 2018 and 2023 in replicated field trial, including 23 experimental lines and three commercial checks, 'Riley's Super Sport', with the commercial name Celebration (U.S. Plant Pat. No. 11,181), 'DT-1' (TifTuf®, U.S. Plant Pat. No. 27,392) and 'Tifway' (unpatented) (shown in Table 1).

Trial at Site One was planted in 2018 in Randomized Complete Block Design (RCBD), with three replicates. Turfgrass quality (1-9; 6=acceptable; 9=highest), leaf texture (1-9; 9=finest), spring greenup (1-9; 9=fastest) and seedhead production (1-9; 9=no seedheads) were evaluated visually, according to National Turfgrass Evaluation Program guidelines (Morris et al. 1998).

TABLE 1

| List of varieties at trial Site One |
|---|
| 'MSB-1012' |
| 'MSB-1017' |
| 'MSB-1026' |
| 'MSB-1041' |
| 'MSB-1042' |
| 'MSB-1044' |
| 'MSB-1046' |
| 'MSB-1047' |
| 'MSB-1048' |
| 'MSB-1050' |
| 'MSB-1059' |
| 'MSB-1067' |
| 'MSB-1069' |
| 'MSB-1072' |
| 'MSB-1073' |
| 'MSB-1074' |
| 'MSB-1075' |
| 'MSB-1076' |
| 'MSB-1077' |
| 'MSB-1078' |
| 'MSB-1079' |
| 'MSB-1080' |
| 'MSB-1081' |
| Celebration ® |
| TifTuf ® |
| Tifway |

Site Two: Trial in Anthony, Florida was conducted between November 2021 and October 2022, in RCBD with three replicates. Turfgrass Quality (1-9; 9=highest; 6=acceptable), Visual Color (1-9; 9=highest), Density (%), Texture (1-9; 9=finest), Normalized Difference Vegetation Index (NDVI; 0-1) was measured with Spectrum Field Scout CM1000 NDVI unit with 5 subsamples per plot, and color determined from NDVI based on the linear regression model converting NDVI units to the more usable/understandable 1-9 color scale (9=darkest) of 'MSB-1080', 'MSB-1017', Celebration® and Tifway were evaluated in this trial. Visual evaluation in Anthony, Florida was also conducted according to National Turfgrass Evaluation Program guidelines.

Patent status of varieties listed herein: 'MSB-1012' unpatented; 'MSB-1017', (U.S. Plant Pat. No. 36,244); 'MSB-1026', unpatented; 'MSB-1041', unpatented; 'MSB-1042', unpatented; 'MSB-1044', unpatented; 'MSB-1046', unpatented; 'MSB-1047', unpatented; 'MSB-1048', unpatented; 'MSB-1050', unpatented; 'MSB-1059', unpatented; 'MSB-1067', unpatented; 'MSB-1069', unpatented; 'MSB-1072', unpatented; 'MSB-1073', unpatented; 'MSB-1074', unpatented; 'MSB-1075', unpatented; 'MSB-1076', unpatented; 'MSB-1077', unpatented; 'MSB-1078', unpatented; 'MSB-1079', unpatented; 'MSB-1080', unpatented; 'MSB-1081', unpatented; 'Riley's Super Sport' with the commercial name Celebration (U.S. Plant Pat. No. 11,181); 'TifTuf', experimental name 'DT-l', (U.S. Plant Pat. No. 27,392); and Tifway, unpatented.

Classification:

*Family*.—Poaceae.

*Species*.—*Cynodon dactylon*.

*Common name*.—Bermudagrass.

*Variety*.—'MSB-1080'.

Parentage:

*Female*.—'MSB-1002' (unpatented).

*Male*.—'MSB 98' (unpatented).

Leaf: The leaf blade of 'MSB-1080' is flat, tapering, with parallel venation and pointed, moderately sharp apex. Adaxial (upper) surface of the leaf is sparsely covered with short, silvery, medium-dense hairs. Hairs on abaxial (bottom) surface are very sparse. Short hairs are present on the leaf margin, ligule is a fringe of hair, collar is narrow and continuous with sparse, short hairs, auricles are absent. Leaf sheath is overlapping. Leaves are folded in the bud. FIG. 2 provides a magnified image of 'MSB-1080' turf in the breeder's block in Starkville, Mississippi. Color of adaxial surface of the leaf matches color 7.5GY/3/4 of the color chart. Abaxial surface matches 7.5GY/3/4. Color of leaf sheath matches 5GY/6/4. Inflorescence with three branches, top half of the culm matching 2.5GY/5/4 on Munsell® Color Chart (1977), bottom half of the culm matching 2.05YR/5/4. When dormant, color of the leaves matches 5Y/8/2 (both sides).

Leaf morphology with measurements of leaf length (mm), leaf width (mm), internode length (mm) and internode diameter (mm) were collected from pots of 'MSB-1017', 'MSB-1042', 'MSB-1050', 'MSB-1080', 'MSB-264', 'Transl', Celebration® and TifTuf®, maintained in the greenhouse in Starkville, Mississippi. The longest leaf at the third node below the apical meristem of the stolon and erect shoot was used for the measurement of leaf length (mm) and leaf width (mm) with digital calipers with four replications. Four random stolons and erect shoots on each pot were measured for internode length (mm) and diameter (mm) between the third and fourth fully extended nodes from the apical meristem. All pots were grown from plugs harvested from Starkville, Mississippi in May 2020. The color of both sides of the leaf blade and leaf sheath was assessed using Munsell® Color Chart (1977) for plant tissue.

In Table 2 below provides a comparison of 'MSB-1080' with seven other grass varieties, including MSU lines and two commercially available cultivars, Celebration® and TifTuf® in the greenhouse. Leaf length of 'MSB-1080' on the erect shoot was similar to Celebration®, 'MSB-1017' and 'MSB-264', wider than leaf length of 'MSB-1050', 'Trans 1' and TifTuf®, and narrower than 'MSB-1042'. Leaves of 'MSB-1080' on erect shoot were narrower than leaves of Celebration®, similar to TifTuf® and wider than all other entries. Internode length of 'MSB-1080' was similar to all entries, except for 'MSB-1042'. Diameter of erect shoot of 'MSB-1080' was smaller than Celebration®, and larger than 'MSB-1050' and 'Trans 1'. Length of leaves of 'MSB-1080' on the stolon was smaller than 'MSB-1042', similar to Celebration® and larger than all other entries. Leaves of 'MSB-1080' growing on the stolons were narrower than Celebration®, wider than 'MSB-264' and 'Trans 1', and similar to all other entries. Internode length of stolon of 'MSB-1080' was similar to 'Trans 1' and shorter than all other entries. Stolon internode diameter was wider than 'Trans 1', narrower than Celebration® and 'MSB-264', and similar to all other entries.

TABLE 2

Leaf length and width, and internode length and diameter of 'MSB-1080', other MSU experimental bermudagrass lines, parental lines (Celebration ® and 'Trans 1') and TifTuf ® measured in the greenhouse (mm).

| | Erect shoot | | | |
|---|---|---|---|---|
| | Leaf | | Internode | |
| Name | Length | Width | Length | Diameter |
| 'MSB-1017' | 39.38 | 2.03 | 13.14 | 0.77 |
| 'MSB-1042' | 57.94 | 1.97 | 21.95 | 0.81 |

TABLE 2-continued

Leaf length and width, and internode length and diameter of 'MSB-1080', other MSU experimental bermudagrass lines, parental lines (Celebration ® and 'Trans 1') and TifTuf ® measured in the greenhouse (mm).

| | | | | |
|---|---|---|---|---|
| 'MSB-1050' | 27.75 | 1.90 | 15.37 | 0.63 |
| 'MSB-1080' | 43.81 | 2.24 | 14.02 | 0.75 |
| 'MSB-264' | 41.50 | 1.79 | 13.12 | 0.77 |
| Celebration ® | 42.00 | 2.58 | 14.97 | 0.94 |
| Trans 1 | 33.38 | 1.60 | 16.85 | 0.49 |
| TifTuf ® | 37.13 | 2.15 | 16.62 | 0.70 |
| LSD | 6.42 | 0.15 | 3.15 | 0.09 |

| | Stolon | | | |
|---|---|---|---|---|
| | Leaf - stolon | | Internode - stolon | |
| Name | Length | Width | Length | Diameter |
| 'MSB-1017' | 15.13 | 2.03 | 40.16 | 1.07 |
| 'MSB-1042' | 33.94 | 1.96 | 30.38 | 0.91 |
| 'MSB-1050' | 9.69 | 2.05 | 42.76 | 0.90 |
| 'MSB-1080' | 22.69 | 2.16 | 12.01 | 0.96 |
| 'MSB-264' | 10.69 | 1.85 | 32.10 | 1.19 |
| Celebration ® | 20.00 | 2.49 | 36.71 | 1.24 |
| Trans 1 | 13.94 | 1.60 | 15.54 | 0.80 |
| TifTuf ® | 16.00 | 2.27 | 25.78 | 1.04 |
| LSD | 4.43 | 0.23 | 5.35 | 0.12 |

In Table 3 below provides a comparison of 'MSB-1080' with six other grass varieties, including male parental line 'MSB 98' and two lines used in developing female parental line 'MSB 1002' (not included in field trials and collection)-Celebration® and 'MS Choice' and three commercially available cultivars, 'Discovery', 'Quickstand' and 'U3' in the field germplasm collection. Field study was conducted in randomized complete block design (RCBD) with three field replicates and 18 leaves and shoots measured in total from each entry. Leaf length of 'MSB-1080' was shorter than male parental line 'MSB 98', 'Discovery', 'MS Choice', and similar to Celebration®, as well as 'Quickstand' and 'U3'. Leaf width of MSB-1080 was similar to 'MSB 98', 'Discovery' and 'U3', and narrower than 'Quickstand'. Internode length of 'MSB-1080' was intermediate between 'MSB 98' and other entries. Internode diameter of 'MSB-1080' was similar to 'MSB 98', 'MS Choice' and 'Quickstand' and intermediate between 'U3' and Celebration® and 'Discovery'.

TABLE 3

Leaf length and width, internode length and diameter of 'MSB-1080', parental lines (MSB 98, Celebration ® and 'MS Choice') and commercial checks measured in the field in Starkville, MS (mm) with letters indicating statistically significant difference between the group means...

| Name | Leaf Length | Leaf width | Internode length | Internode diameter |
|---|---|---|---|---|
| Celebration ® | 41.87 abc | 2.26 c | 32.40 b | 1.55 a |
| 'MS Choice' | 35.93 bcd | 2.69 ab | 31.47 b | 1.41 ab |
| 'Discovery' | 27.13 d | 2.41 bc | 27.40 b | 1.56 a |
| 'MSB 98' | 34.60 cd | 2.51 bc | 47.20 a | 1.38 ab |
| 'MSB-1080' | 47.47 ab | 2.37 bc | 38.93 ab | 1.46 ab |
| 'Quickstand' | 48.80 a | 3.02 a | 31.07 b | 1.40 ab |
| 'U3' | 39.07 abcd | 2.45 bc | 29.27 b | 1.30 b |
| SE | 2.94 | 0.08 | 2.74 | 0.05 |
| CV | 29.04 | 12.91 | 31.22 | 12.89 |
| P-value | 0.001 | 0.001 | 0.001 | 0.01 |

In Table 4 below shows turfgrass quality (TQ) of 'MSB-1080' evaluated visually on a scale 1 to 9, with 9=highest and 6=acceptable quality, in Starkville, Mississippi was high, with mean quality of $\bar{x}$TQ=6.7 across six years. It was similar to TifTuf®, 'MSB-1017' and 'MSB-1050' and greater than Celebration®, 'Tifway' and most of other experimental Mississippi State University entries. In each year of the study 'MSB-1080' retained mean quality above acceptable level (TQ=6). In years 2021-2023 'MSB-1080' placed in top statistical group for mean turfgrass quality (shown in Table 4). In Anthony, Florida, 'MSB-1080' bad the greatest quality ($\bar{x}$TQ=7.39), slightly greater, but similar to Celebration® ($\bar{x}$TQ=7.15) and MSB-1017 (TQ=$\bar{x}$7.29) and significantly higher than Tifway ($\bar{x}$TQ=6.90) (see Table 9 below).

TABLE 4

Turfgrass quality, evaluated visually (1-9; 6 = acceptable; 9 = highest), of 23 experimental bermudagrass entries and three commercial checks evaluated at Mississippi State University in 2018-2023, Starkville, MS.

| | Turfgrass Quality | | |
|---|---|---|---|
| Name | 2018 | 2019 | 2020 |
| 'MSB-1012' | 5.3 efghij | 5.3 defghi | 5.7 fghi |
| 'MSB-1017' | 6.6 abcd | 6.0 bcd | 6.8 ab |
| 'MSB-1026' | 6.6 abcd | 6.3 ab | 6.3 bcdef |
| 'MSB-1041' | 5.7 defghi | 5.5 cdefgh | 5.9 cdefg |
| 'MSB-1042' | 6.2 bcde | 5.9 bcde | 6.3 bcdef |
| 'MSB-1044' | 6.1 bcdef | 5.8 bcdef | 6.4 bcd |
| 'MSB-1046' | 5.8 cdefgh | 5.7 bcdefg | 6.8 ab |
| 'MSB-1047' | 5.4 efghij | 5.0 fghijk | 6.4 bcde |
| 'MSB-1048' | 6.6 abcd | 6.0 bcd | 6.8 ab |
| 'MSB-1050' | **7.2 a** | **6.9 a** | **7.2 a** |
| 'MSB-1059' | 5.9 cdefg | 5.0 fghijk | 5.3 ghij |
| 'MSB-1067' | 4.9 hij | 5.7 bcdefg | 5.8 defgh |
| 'MSB-1069' | 3.6 l | 5.1 efghij | 5.6 ghi |
| 'MSB-1072' | 4.6 jk | 4.2 kl | 5.0 ijk |
| 'MSB-1073' | 5.2 fghij | 4.5 ijk | 5.2 ghij |
| 'MSB-1074' | 4.8 hij | 4.7 hijk | 4.7 jkl |
| 'MSB-1075' | 6.3 abcde | 5.8 bcdef | 6.5 bc |
| 'MSB-1076' | 4.8 ijk | 4.3 jkl | 4.3 klm |
| 'MSB-1077' | 5.1 ghij | 4.9 ghijk | 5.2 hij |
| 'MSB-1078' | 4.5 jkl | 4.3 kl | 4.2 lm |
| 'MSB-1079' | 5.9 cdefg | 5.3 defghi | 5.7 efgh |
| 'MSB-1080' | 6.4 abcd | 6.1 abc | 6.8 ab |
| 'MSB-1081' | 3.8 kl | 3.6 l | 3.9 m |
| Celebration ® | 5.4 efghij | 5.0 fghijk | 5.7 fghi |
| TifTuf ® | 6.9 ab | 6.1 bcd | 6.5 bc |
| Tifway | 6.8 abc | 5.9 bcde | 6.4 bcd |
| SEM | 0.2 | 0.2 | 0.1 |
| CV | 11.0 | 11.5 | 10.0 |
| P - value | 0.001 | 0.001 | 0.001 |

| | Turfgrass Quality | | |
|---|---|---|---|
| Name | 2021 | 2022 | 2023 |
| 'MSB-1012' | 5.6 bcd | 5.5 Hij | 4.9 ghijk |
| 'MSB-1017' | **6.4 a** | 6.9 Abc | 6.6 ab |
| 'MSB-1026' | 6.1 abc | 6.7 Abcd | 6.3 abcd |
| 'MSB-1041' | 5.4 cde | 5.9 Efghi | 5.4 cdefgh |
| 'MSB-1042' | 6.2 ab | 6.0 Efgh | 6.5 ab |
| 'MSB-1044' | 6.1 abc | 5.8 Fghi | 6.0 abcdef |
| 'MSB-1046' | 6.3 ab | 6.4 Bcde | 6.3 abc |
| 'MSB-1047' | 6.1 abc | 6.0 Efgh | 5.3 defghi |
| 'MSB-1048' | **6.5 a** | 6.4 Bcde | 6.5 ab |
| 'MSB-1050' | **6.5 a** | 6.8 abcd | 6.5 ab |
| 'MSB-1059' | 5.4 cde | 4.8 kl | 5.1 fghij |
| 'MSB-1067' | 5.7 bcd | 5.1 jk | 5.4 cdefgh |
| 'MSB-1069' | 5.6 bcd | 5.5 hij | 5.7 bcdefg |
| 'MSB-1072' | 4.4 fg | 4.7 kl | 3.9 klmn |
| 'MSB-1073' | 5.2 def | 5.0 jk | 4.3 jklm |

TABLE 4-continued

Turfgrass quality, evaluated visually (1-9; 6 = acceptable; 9 = highest), of 23 experimental bermudagrass entries and three commercial checks evaluated at Mississippi State University in 2018-2023, Starkville, MS.

| | | | |
|---|---|---|---|
| 'MSB-1074' | 4.3 g | 4.3 lm | 4.4 ijklm |
| 'MSB-1075' | 6.3 ab | 6.3 defg | 5.5 cdefgh |
| 'MSB-1076' | 4.3 g | 4.1 mn | 3.9 lmn |
| 'MSB-1077' | 4.8 efg | 4.8 kl | 4.6 hijkl |
| 'MSB-1078' | 3.3 h | 3.8 n | 3.5 mn |
| 'MSB-1079' | 5.3 de | 5.8 ghi | 5.1 fghij |
| 'MSB-1080' | **6.8 a** | **7.0 a** | **6.8 a** |
| 'MSB-1081' | 3.3 h | 3.9 mn | 3.2 n |
| Celebration ® | 5.7 bcd | 5.5 ij | 5.3 efghij |
| TifTuf ® | **6.5 a** | 7.0 ab | **6.7 a** |
| Tifway | **6.4 a** | 6.4 cdef | 6.1 abcde |
| SEM | 0.1 | 0.1 | 0.2 |
| CV | 11.1 | 9.7 | 13.1 |
| P - value | 0.001 | 0.001 | 0.001 |

SEM - Standard Error of Means; CV - Coefficient of Variation (%); P - probability value
Data were analyzed using Analysis of Variance with Tukey's honest significant difference (HSD) test (P = 0.05), with letters indicating statistically significant difference between the group means. Means followed by the same letter in a column are not significantly different at P indicated in the table.
Values in the top statistical group are bolded.

In Table 5 below shows 'MSB-1080' had medium-fine leaf texture (LT), between 6.3 and 7.0 (mean LT across years=6.8; Table 5 & 8). In 2018 MSU trial its mean texture was finer than Celebration® and TifTuf®, but coarser than 'MSB-1017' ($\bar{x}$LT=7.0), 'MSB-1048' ($\bar{x}$LT=7.1) and 'MSB-1050' ($\bar{x}$LT=8.3). Texture of 'MSB-1080' ($\bar{x}$LT=7.9) in Anthony, FL, was significantly finer than Tifway ($\bar{x}$LT=5.9), similar to Celebration® ($\bar{x}$LT=7.0) and coarser than MSB-1017 ($\bar{x}$LT=7.9) (see Table 9).

TABLE 5

Leaf texture, evaluated visually (1-9; 9 = finest), of 23 experimental bermudagrass entries and three commercial checks evaluated at Mississippi State University in 2018-2023, Starkville, MS.

| | Leaf Texture | | | | |
|---|---|---|---|---|---|
| Name | 2018 | 2020 | 2021 | 2022 | 2023 |
| 'MSB-1012' | 6.0 cde | 5.5 efgh | 5.0 de | 6.0 bc | 5.5 defg |
| 'MSB-1017' | 7.0 b | 7.0 b | 7.0 ab | 7.0 b | 7.0 bc |
| 'MSB-1026' | 6.7 bc | 6.3 bcde | 6.0 bcde | 7.0 b | 6.2 bcdefg |
| 'MSB-1041' | 6.0 cde | 5.8 defg | 5.3 cde | 6.0 bc | 6.0 cdefg |
| 'MSB-1042' | 7.0 b | 6.7 bcd | 6.3 bcd | 6.3 bc | 6.7 bcd |
| 'MSB-1044' | 6.0 cde | 6.3 bcde | 6.0 bcde | 6.0 bc | 6.3 bcdef |
| 'MSB-1046' | 6.3 bcd | 6.7 bcd | 6.3 bcd | 6.7 b | 6.5 bcde |
| 'MSB-1047' | 5.0 f | 6.0 cdef | 6.0 bcde | 6.0 bc | 5.7 defg |
| 'MSB-1048' | 7.0 b | 7.0 b | 7.0 ab | 7.0 b | 7.3 ab |
| 'MSB-1050' | **8.0 a** | **8.0 a** | **8.0 a** | **9.0 a** | **8.5 a** |
| 'MSB-1059' | 6.7 bc | 6.0 bcde | 6.3 bcd | 6.3 bc | 6.3 bcdef |
| 'MSB-1067' | 6.0 cde | 6.2 bcde | 6.0 bcde | 6.0 bc | 6.7 bcd |
| 'MSB-1069' | 6.0 cde | 6.3 bcde | 6.0 bcde | 6.3 bc | 6.2 bcdefg |
| 'MSB-1072' | 5.0 f | 5.2 fgh | 5.3 cde | 6.0 bc | 5.0 g |
| 'MSB-1073' | 5.3 ef | 5.0 gh | 5.7 bcde | 6.0 bc | 5.3 efg |
| 'MSB-1074' | 6.0 cde | 5.2 fgh | 4.7 e | 6.0 bc | 5.8 cdefg |
| 'MSB-1075' | 6.0 cde | 6.7 bcd | 6.7 abc | 6.7 b | 6.5 bcde |
| 'MSB-1076' | 6.0 cde | 5.8 defg | 6.3 bcd | 6.0 bc | 5.2 fg |
| 'MSB-1077' | 6.0 cde | 5.7 efg | 5.3 cde | 6.0 bc | 5.7 defg |
| 'MSB-1078' | 5.7 def | 5.5 efgh | 5.3 cde | 6.0 bc | 5.7 defg |
| 'MSB-1079' | 6.7 bc | 6.2 bcde | 6.3 bcd | 6.3 bc | 6.5 bcde |
| 'MSB-1080' | 6.3 bcd | 6.8 bc | 7.0 ab | 7.0 b | 6.7 bcd |

TABLE 5-continued

Leaf texture, evaluated visually (1-9; 9 = finest), of 23 experimental bermudagrass entries and three commercial checks evaluated at Mississippi State University in 2018-2023, Starkville, MS.

| | Leaf Texture | | | | |
|---|---|---|---|---|---|
| Name | 2018 | 2020 | 2021 | 2022 | 2023 |
| 'MSB-1081' | 5.0 f | 4.7 h | 4.7 e | 5.3 c | 5.7 defg |
| Celebration ® | 5.0 f | 5.0 gh | 5.7 bcde | 6.0 bc | 5.5 defg |
| Tiftuf ® | 6.0 cde | 6.2 bcde | 6.7 abc | 6.3 bc | 6.0 cdefg |
| Tifway | 6.0 cde | 6.2 bcde | 6.3 bcd | 6.7 b | 6.3 bcdef |
| SEM | 0.2 | 0.2 | 0.3 | 0.2 | 0.2 |
| CV | 4.9 | 7.0 | 7.5 | 5.3 | 9.0 |
| P - value | 0.001 | 0.001 | 0.001 | 0.001 | 0.001 |

SEM—Standard Error of Means; CV—Coefficient of Variation (%); P—probability value
Data were analyzed using Analysis of Variance with Tukey's honest significant difference (HSD) test (P = 0.05), with letters indicating statistically significant difference between the group means. Means followed by the same letter in a column are not significantly different at P indicated in the table.
Values in the top statistical group are bolded.

In Table 6 below shows mean spring greenup (SG) of 'MSB-1080' in 2018MSU trial across all years was 5.2 (please see Table 8), similar to 'MSB-1069' ($\bar{x}$SG=5.3), slower than 'MSB-1042' ($\bar{x}$SG=5.8), 'MSB-1046' ($\bar{x}$SG=5.8) and TifTuf® ($\bar{x}$SG=5.5), and faster than Celebration® and most other experimental lines. Variation in spring greenup was high between years (please see Table 6), but in all years Spring Greenup of 'MSB-1080' evaluated at MSU was fast, placing it among top performers: TifTuf®, 'MSB-1026', 'MSB-1042', 'MSB-1046' and 'MSB-1069'. In 2022, 'MSB-1080' was together with TifTuf® the fastest to green up (both $\bar{x}$SG-6.0).

TABLE 6

Spring greenup, evaluated visually (1-9; 9 = fastest), of 23 experimental bermudagrass entries and three commercial checks evaluated at Mississippi State University in 2018-2023, Starkville, MS.

| | Spring Greenup | | | | |
|---|---|---|---|---|---|
| Name | 2019 | 2020 | 2021 | 2022 | 2023 |
| 'MSB-1012' | 3.0 abc | 4.3 abcde | 4.3 cdef | 5.0 abc | 4.0 bcdef |
| 'MSB-1017' | 3.0 abc | 5.0 abc | 5.0 abcde | 5.7 ab | 5.3 abcde |
| 'MSB-1026' | 2.7 abcd | **5.7 a** | 5.0 abcde | 5.7 ab | 6.3 abc |
| 'MSB-1041' | 2.7 abcd | 4.3 abcde | 4.3 cdef | 5.3 abc | 4.0 bcdef |
| 'MSB-1042' | 4.0 ab | 5.3 ab | 6.7 ab | 5.7 ab | **7.3 a** |
| 'MSB-1044' | 4.0 ab | 5.0 abc | 6.0 abc | 5.0 abc | 5.3 abcde |
| 'MSB-1046' | **4.3 a** | **5.7 a** | **7.0 a** | 5.7 ab | 6.3 abc |
| 'MSB-1047' | 3.7 abc | 4.7 abcd | 5.7 abc | 5.7 ab | 4.3 bcdef |
| 'MSB-1048' | 2.0 cd | 4.0 bcde | 5.0 abcde | 4.3 abc | 5.3 abcde |
| 'MSB-1050' | 2.7 abcd | 4.0 bcde | 3.0 ed | 4.3 abc | 4.0 bcdef |
| 'MSB-1059' | 2.3 bcd | 3.0 ef | 3.3 def | 2.3 d | 4.0 bcdef |
| 'MSB-1067' | 3.3 abc | 4.7 abcd | 5.3 abcd | 4.7 abc | 5.0 abcde |
| 'MSB-1069' | 3.3 abc | 5.0 abc | **7.0 a** | 5.3 abc | 5.7 abcd |
| 'MSB-1072' | 3.0 abc | 4.0 bcde | 4.0 cdef | 3.7 cd | 3.0 def |
| 'MSB-1073' | 3.3 abc | 4.0 bcde | 5.0 abcde | 4.3 abc | 3.7 cdef |
| 'MSB-1074' | 3.0 abc | 3.7 cdef | 4.7 bcde | 3.7 cd | 3.7 cdef |
| 'MSB-1075' | 3.7 abc | 4.0 bcde | 5.0 abcde | 4.7 abc | 4.0 bcdef |
| 'MSB-1076' | 2.7 abcd | 3.3 def | 4.3 cdef | 3.7 cd | 2.7 ef |
| 'MSB-1077' | 2.7 abcd | 4.0 bcde | 4.0 cdef | 3.7 cd | 3.0 def |
| 'MSB-1078' | 2.7 abcd | 4.0 bcde | 3.0 ed | 3.7 cd | 2.7 ef |
| 'MSB-1079' | 3.7 abc | 4.3 abcde | 4.7 bcde | 5.0 abc | 4.0 bcdef |
| 'MSB-1080' | 3.0 abc | 5.0 abc | 6.0 abc | **6.0 a** | 6.0 abc |

TABLE 6-continued

Spring greenup, evaluated visually (1-9; 9 = fastest), of 23 experimental bermudagrass entries and three commercial checks evaluated at Mississippi State University in 2018-2023, Starkville, MS.

| | Spring Greenup | | | | |
|---|---|---|---|---|---|
| Name | 2019 | 2020 | 2021 | 2022 | 2023 |
| 'MSB-1081' | 1.0 d | 2.3 f | 2.3 f | 4.0 bcd | 2.0 f |
| Celebration ® | 3.7 abc | 4.7 abcd | 5.0 abcde | 5.0 abc | 4.3 bcdef |
| Tiftuf ® | 3.3 abc | 5.3 ab | 6.0 abc | **6.0 a** | 6.7 ab |
| Tifway | 3.3 abc | 4.3 abcde | 5.7 abc | 5.3 abc | 4.0 bcdef |
| SEM | 0.3 | 0.3 | 0.4 | 0.3 | 0.5 |
| CV | 18.8 | 11.6 | 13.7 | 11.2 | 19.4 |
| P - value | 0.001 | 0.001 | 0.001 | 0.001 | 0.001 |

SEM—Standard Error of Means; CV—Coefficient of Variation (%); P—probability value
Data were analyzed using Analysis of Variance with Tukey's honest significant difference (HSD) test (P = 0.05), with letters indicating statistically significant difference between the group means. Means followed by the same letter in a column are not significantly different at P indicated in the table.
Values in the top statistical group are Values in the top statistical group are bolded..

In Table 7 below shows Seedhead production (SP), evaluated visually on a scale 1 to 9, with 9=lowest SP, varied among entries. 'MSB-1080' in MSU 2018 trial produced seedheads, however intensity was low, with mean SP across years of 8.1 (please see Table 8). This was the same as Tifway ($\bar{x}$SP=8.3), 'MSB-1017' ($\bar{x}$SP=8.3) and 'MSB-1042' ($\bar{x}$SP=8.3), and similar to 'MSB-1044' ($\bar{x}$SP=7.9), 'MSB-1048' ($\bar{x}$SP=8.0) and 'MSB-1069' ($\bar{x}$SP=8.0). It was higher than 'MSB-1026', which did not produce any seedheads ($\bar{x}$SP=9.0), 'MSB-1050' ($\bar{x}$SP=8.8) and 'MSB-1041' ($\bar{x}$SP=8.7), but lower than Celebration® ($\bar{x}$SP=5.9) and most other MSU experimental lines.

TABLE 7

Seedhead production, evaluated visually (1-9; 9 = no seedheads), of 23 experimental bermudagrass entries and three commercial checks evaluated at Mississippi State University in 2018-2023, Starkville, MS.

| | Seedhead production | | |
|---|---|---|---|
| Name | 2018 | 2019 | 2020 |
| 'MSB-1012' | 8.3 ab | 7.1 cde | 6.7 cd |
| 'MSB-1017' | 9.0 a | 7.0 cde | 8.2 ab |
| 'MSB-1026' | 9.0 a | 9.0 a | 9.0 a |
| 'MSB-1041' | 8.7 a | 8.7 ab | 8.7 ab |
| 'MSB-1042' | 8.7 a | 7.2 bcde | 8.1 ab |
| 'MSB-1044' | 9.0 a | 6.8 defg | 8.1 ab |
| 'MSB-1046' | 8.8 a | 7.1 cde | 8.5 ab |
| 'MSB-1047' | 8.8 a | 5.4 fghij | 7.7 bc |
| 'MSB-1048' | 8.5 a | 6.4 defgh | 8.0 ab |
| 'MSB-1050' | 9.0 a | 7.7 abcde | 8.7 ab |
| 'MSB-1059' | 9.0 a | 6.2 efghi | 7.5 bc |
| 'MSB-1067' | 9.0 a | 8.3 abc | 8.3 ab |
| 'MSB-1069' | 9.0 a | 6.9 cdef | 8.1 ab |
| 'MSB-1072' | 6.3 cd | 5.2 hij | 5.7 de |
| 'MSB-1073' | 7.8 abc | 4.9 ij | 5.9 de |
| 'MSB-1074' | 5.5 de | 4.9 ij | 4.9 ef |
| 'MSB-1075' | 8.2 ab | 7.8 abcd | 9.0 a |
| 'MSB-1076' | 4.5 de | **4.6 j** | **4.3 f** |
| 'MSB-1077' | 6.0 de | 5.3 ghij | 5.3 ef |
| 'MSB-1078' | 5.3 de | **4.6 j** | 4.7 ef |
| 'MSB-1079' | 6.3 cd | 5.0 hij | 5.4 def |
| 'MSB-1080' | 7.8 abc | 6.8 defg | 8.5 ab |
| 'MSB-1081' | 6.0 de | 4.8 ij | 5.2 ef |
| Celebration ® | 6.8 bcd | 4.9 ij | 5.7 de |
| Tiftuf ® | 8.0 ab | 6.8 defg | 7.6 bc |
| Tifway | 9.0 a | 7.3 abcd | 8.5 ab |
| SEM | 0.3 | 0.3 | 0.3 |
| CV | 9.8 | 13.4 | 13.7 |

TABLE 7-continued

Seedhead production, evaluated visually (1-9; 9 = no seedheads), of 23 experimental bermudagrass entries and three commercial checks evaluated at Mississippi State University in 2018-2023, Starkville, MS.

| P | 0.001 | 0.001 | 0.001 |
|---|---|---|---|
| | Seedhead production | | |
| Name | 2021 | 2022 | 2023 |
| 'MSB-1012' | 7.0 bcde | 6.7 efg | 6.9 fgh |
| 'MSB-1017' | 8.1 ab | 8.7 ab | 8.5 abcd |
| 'MSB-1026' | 9.0 a | 9.0 a | 9.0 a |
| 'MSB-1041' | 8.4 ab | 8.7 ab | 8.7 abc |
| 'MSB-1042' | 8.0 ab | 8.6 ab | 8.8 ab |
| 'MSB-1044' | 7.8 abc | 8.2 abc | 7.7 bcdef |
| 'MSB-1046' | 7.9 ab | 8.2 abc | 8.1 abcdef |
| 'MSB-1047' | 7.4 abcd | 8.2 abcd | 7.1 efg |
| 'MSB-1048' | 8.3 ab | 8.5 ab | 7.9 abcdef |
| 'MSB-1050' | 8.9 a | 9.0 a | 8.9 ab |
| 'MSB-1059' | 6.9 bcde | 7.6 bcde | 7.5 cde |
| 'MSB-1067' | 8.3 ab | 8.4 abc | 8.7 abc |
| 'MSB-1069' | 7.8 abc | 8.3 abc | 8.1 abcdef |
| 'MSB-1072' | 5.5 ed | 7.0 def | **5.3 i** |
| 'MSB-1073' | 6.1 cdef | 7.2 cde | 6.0 ghi |
| 'MSB-1074' | **4.9 f** | 5.7 gh | 6.1 ghi |
| 'MSB-1075' | 8.4 ab | 8.7 ab | 8.4 abcde |
| 'MSB-1076' | **4.5 f** | 5.6 gh | 5.8 hi |
| 'MSB-1077' | 5.3 ef | 5.8 fgh | **5.5 i** |
| 'MSB-1078' | 5.5 ef | **4.9 h** | 5.7 hi |
| 'MSB-1079' | 5.5 ef | 6.7 efg | **5.3 i** |
| 'MSB-1080' | 7.8 abc | 8.6 ab | 8.0 abcdef |
| 'MSB-1081' | **4.9 f** | **4.9 h** | 6.1 ghi |
| Celebration ® | 5.9 def | 6.6 efg | **5.3 i** |
| Tiftuf ® | 7.4 abcd | 8.3 abc | 7.2 defg |
| Tifway | 7.9 ab | 8.6 ab | 8.1 abcdef |
| SEM | 0.3 | 0.2 | 0.2 |
| CV | 18.2 | 14.8 | 12.9 |
| P | 0.001 | 0.001 | 0.001 |

SEM - Standard Error of Means; CV - Coefficient of Variation (%); P - probability value
Data were analyzed using Analysis of Variance with Tukey's honest significant difference (HSD) test (P = 0.05), with letters indicating statistically significant difference between the group means. Means followed by the same letter in a column are not significantly different at P indicated in the table.
Values in the top statistical group are bolded.

In Table 8 below provides an overall summary of the mean turfgrass quality, leaf texture, spring greenup, and seedhead production across six years (2018-2023) of 23 experimental bermudagrass entries and three commercial checks evaluated at Starkville, Mississippi.

TABLE 8

Mean Turfgrass Quality (1-9; 9 = highest; 6 = acceptable), Leaf Texture (1-9; 9 = finest), Spring greenup (1-9; 9 = fastest), and Seedhead production (1-9; 9 = no seedheads) across six years (2018-2023) of 23 experimental bermudagrass entries and three commercial checks evaluated at Mississippi State University, Starkville, MS.

| Name | Turfgrass Quality | Leaf Texture | Spring Greenup | Seedhead Production |
|---|---|---|---|---|
| 'MSB-1012' | 5.4 hi | 5.6 ijk | 4.1 bcdefgh | 7.0 gh |
| 'MSB-1017' | 6.6 abc | 7.0 bc | 4.8 abcde | 8.3 bcd |
| 'MSB-1026' | 6.4 bcd | 6.4 def | 5.1 abcd | **9.0 a** |
| 'MSB-1041' | 5.7 gh | 5.9 fghi | 4.1 bcdefgh | 8.7 abc |
| 'MSB-1042' | 6.2 de | 6.6 bcde | **5.8 a** | 8.3 bcd |
| 'MSB-1044' | 6.0 ef | 6.2 efgh | 5.1 abcd | 7.9 def |
| 'MSB-1046' | 6.3 cde | 6.5 cde | **5.8 a** | 8.1 bcde |
| 'MSB-1047' | 5.8 fg | 5.8 ghij | 4.8 abcde | 7.5 efg |
| 'MSB-1048' | 6.5 bcd | 7.1 b | 4.1 bcdefgh | 8.0 cdef |
| 'MSB-1050' | **6.9 a** | **8.3 a** | 3.6 efghi | 8.8 ab |
| 'MSB-1059' | 5.2 ij | 6.3 defg | 3.0 hi | 7.4 fg |
| 'MSB-1067' | 5.4 hi | 6.2 defgh | 4.6 abcdef | 8.5 abcd |

TABLE 8-continued

Mean Turfgrass Quality (1-9; 9 = highest; 6 = acceptable), Leaf Texture (1-9; 9 = finest), Spring greenup (1-9; 9 = fastest), and Seedhead production (1-9; 9 = no seedheads) across six years (2018-2023) of 23 experimental bermudagrass entries and three commercial checks evaluated at Mississippi State University, Starkville, MS.

| Name | Turfgrass Quality | Leaf Texture | Spring Greenup | Seedhead Production |
|---|---|---|---|---|
| 'MSB-1069' | 5.3 i | 6.2 efgh | 5.3 abc | 8.0 cdef |
| 'MSB-1072' | 4.5 k | 5.2 jk | 3.5 efghi | 5.9 ij |
| 'MSB-1073' | 4.9 j | 5.4 ijk | 4.1 cdefgh | 6.3 hi |
| 'MSB-1074' | 4.5 k | 5.5 ijk | 3.7 defgh | 5.4 jklm |
| 'MSB-1075' | 6.1 de | 6.5 cde | 4.3 bcdefgh | 8.5 abcd |
| 'MSB-1076' | 4.3 k | 5.8 ghij | 3.3 fghi | 5.0 m |
| 'MSB-1077' | 4.9 j | 5.7 hij | 3.5 efghi | 5.5 jklm |
| 'MSB-1078' | 3.9 l | 5.6 ijk | 3.2 ghi | 5.1 1m |
| 'MSB-1079' | 5.5 ghi | 6.4 def | 4.3 bcdefgh | 5.8 ijkl |
| 'MSB-1080' | 6.7 ab | 6.8 bcd | 5.2 abc | 81 ede |
| 'MSB-1081' | 3.6 l | 5.1 k | 2.3 i | 5.2 klm |
| Celebration ® | 5.4 hi | 5.4 ijk | 4.5 abcdefg | 5.9 ijk |
| Tiftuf ® | 6.6 abc | 6.2 efgh | 5.5 ab | 7.6 efg |
| Tifway | 6.3 cde | 6.3 defg | 4.5 abcdefg | 8.3 bcd |
| SEM | 0.1 | 0.1 | 0.3 | 0.1 |
| CV | 12.0 | 8.0 | 23.5 | 15.9 |
| P | 0.001 | 0.001 | 0.001 | 0.001 |

SEM—Standard Error of Means; CV—Coefficient of Variation (%); P—probability value Data were analyzed using Analysis of Variance with Tukey's honest significant difference (HSD) test (P = 0.05), with letters indicating statistically significant difference between the group means. Means followed by the same letter in a column are not significantly different at P indicated in the table.

Values in the top statistical group are bolded.

COMPARISON WITH KNOWN VARIETIES

In Table 9 below provides a comparison of 'MSB-1080' with the commercial lines 'MSB-1017', Celebration® and Tifway.

In Anthony, Florida, as shown in Table 9 below, both 'MSB-1080' and 'MSB-1017' had very high density, expressed as a percent of ground cover (mean density 99.2% and 99.6% respectively, Table 8), greater than Celebration® ($\bar{x}$ density=98.2%) and Tifway ($\bar{x}$ density=97.4%).

Normalized Difference Vegetation Index (0-1) of all four lines in Anthony, Florida was high, please see Table 9 below. 'MSB-1080' had NDVI=0.83, similar to 'MSB-1017' (0.84) and higher than Celebration® and Tifway (both 0.80).

Mean color of 'MSB-1080' evaluated visually on a scale 1 to 9, with 9=darkest green, in Anthony, Florida, was similar to 'MSB-1017' ($\bar{x}$TQ=7.54 and 7.47, for 'MSB-1080' and 'MSB-1017', respectively; Table 9 below), and darker than Celebration® and Tifway ($\bar{x}$TQ=7.31 and 7.13, respectively). Color derived from NDVI measurements, expressed on a scale 1 to 9, with 9=darkest green, was slightly lighter than assessed visually. 'MSB-1080' was similar to 'MSB-1017' ($\bar{x}$TQ=7.22 and 7.30, respectively), similarly to visually assessed color, and higher than Celebration® ($\bar{x}$TQ=6.88) and Tifway ($\bar{x}$TQ=6.82).

TABLE 9

Turfgrass Quality (1-9; 9 = highest; 6 = acceptable), Visual Color (1-9; 9 = highest), Density (%), Leaf Texture (1-9; 9 = finest), NDVI (0-1), and Color derived from NDVI (1-9; 9 = darkest) of 'MSB-1080', 'MSB-1017', Celebration ® and 'Tifway' evaluated at Southeastern Turfgrass Research Center, Anthony, FL between November 2021 and October 2022.

| Name | Turfgrass Quality | Visual Color | Density |
|---|---|---|---|
| 'MSB-1017' | 7.29 ab | 7.47 ab | **99.64 a** |
| 'MSB-1080' | **7.39 a** | **7.54 a** | **99.22 a** |
| Celebration ® | 7.15 ab | 7.31 ab | 98.22 b |
| Tifway | 6.90 b | 7.13 b | 97.44 b |
| SEM | 0.12 | 0.11 | 0.26 |
| CV | 9.81 | 8.74 | 1.59 |
| P - value | 0.025 | 0.03 | 0.001 |

| Name | Leaf Texture | NDVI | NDVI Color |
|---|---|---|---|
| 'MSB-1017' | **7.89 a** | **0.84 a** | **7.30 a** |
| 'MSB-1080' | 7.06 b | **0.83 a** | **7.22 a** |
| Celebration ® | 7.00 b | 0.80 b | 6.88 b |
| Tifway | 5.92 c | 0.80 b | 6.82 b |
| SEM | 0.06 | 0.00 | 0.05 |
| CV | 5.18 | 6.80 | 8.40 |
| P - value | 0.001 | 0.001 | 0.001 |

SEM - Standard Error of Means; CV - Coefficient of Variation (%); P - probability value Data were analyzed using Analysis of Variance with Tukey's honest significant difference (HSD) test (P = 0.05), with letters indicating statistically significant difference between the group means. Means followed by the same letter in a column are not significantly different at P indicated in the table.

Values in the top statistical group are bolded.

FIG. 4. is a pictorial representation of a phylogenetic tree that shows 'MSB-1080' is genetically different from the other bermudagrass cultivars analyzed.

Genetic diversity study was conducted using genotyping by sequencing (GBS). Twenty-one experimental lines and six commercially available cultivars [Celebration®; MS Choice; Discovery™, Barazur (De Bruijn, 2012); Quickstand and U3 (Hanson, 1972)] were included in the study. DNA libraries were sequenced with 101 bp single end reads on an Illumina Novaseq SP platform. Genetic distance matrix was calculated using fixation index ($F_{st}$) in R adegenet package (Jombart et al., 2010; Jombart and Ahmed, 2011), and used to construct a Neighbor-Joining dendrogram in Interactive Tree Of Life (iTOL) v5 (Letunic and Bork, 2021).

COMPARISON WITH PARENTAL LINES

'MSB-1080' can be distinguished from the Celebration® and 'MS Choice'—lines used in developing the female parent 'MSB 1002', in that 'MSB-1080' has shorter leaves than both 'Celebration' and 'MS Choice', and smaller internode diameter than Celebration®. 'MSB-1080' has also higher visual turfgrass quality scores, finer leaf texture evaluated visually on a scale 1 to 9, and less seed head production than Celebration®.

'MSB-1080' can be distinguished from the male parent 'MSB 98' in that 'MSB-1080' has shorter leaves.

In Table 10 below shows a comparison of the Genetic distance matrix ($F_{st}$) of 'MSB-1080', 17 other lines, including the male parent 'MSB 98' and five commercial checks based on Singel Nucleotide Polymorphism (SNP) markers.

TABLE 10

Genetic distance matrix ($F_{st}$) of 'MSB-1080', 17 other lines from Mississippi State University and five commercial checks based on Single Nucleotide Polymorphism (SNP) markers.

| Taxa | Celebration | Choice | Discovery | MSU105 | MSU1080 |
|---|---|---|---|---|---|
| Celebration | 0 | 0.25 | 0.17 | 0.23 | 0.24 |
| Choice | 0.25 | 0 | 0.25 | 0.23 | 0.27 |
| Discovery | 0.17 | 0.25 | 0 | 0.23 | 0.24 |
| MSB-105 | 0.23 | 0.23 | 0.23 | 0 | 0.24 |
| **MSB-1080** | **0.24** | **0.27** | **0.24** | **0.24** | **0** |
| MSB-109 | 0.25 | 0.2 | 0.25 | 0.22 | 0.26 |
| MSB-112 | 0.25 | 0.19 | 0.25 | 0.21 | 0.25 |
| MSB-116 | 0.25 | 0.28 | 0.25 | 0.19 | 0.22 |
| MSB-125 | 0.26 | 0.29 | 0.26 | 0.22 | 0.21 |
| MSB-154 | 0.25 | 0.27 | 0.25 | 0.21 | 0.23 |
| MSB-1541 | 0.25 | 0.27 | 0.25 | 0.22 | 0.23 |
| MSB-1542 | 0.24 | 0.24 | 0.24 | 0.23 | 0.23 |
| MSB-178 | 0.25 | 0.25 | 0.25 | 0.24 | 0.22 |
| MSB-278 | 0.27 | 0.3 | 0.27 | 0.23 | 0.23 |
| MSB-74 | 0.25 | 0.27 | 0.25 | 0.21 | 0.22 |
| MSB-75 | 0.26 | 0.29 | 0.26 | 0.23 | 0.21 |
| MSB-91 | 0.25 | 0.28 | 0.25 | 0.21 | 0.22 |
| MSB-97 | 0.25 | 0.19 | 0.25 | 0.23 | 0.26 |
| MSB 98 | 0.25 | 0.25 | 0.25 | 0.24 | 0.22 |
| Quickstand | 0.28 | 0.22 | 0.28 | 0.26 | 0.3 |
| Trans1 | 0.3 | 0.33 | 0.3 | 0.3 | 0.26 |
| Trans2 | 0.3 | 0.33 | 0.3 | 0.31 | 0.26 |
| U3 | 0.28 | 0.26 | 0.29 | 0.3 | 0.3 |

| Taxa | MSU109 | MSU112 | MSU116 | MSU125 | MSU154 |
|---|---|---|---|---|---|
| Celebration | 0.25 | 0.25 | 0.25 | 0.26 | 0.25 |
| Choice | 0.2 | 0.19 | 0.28 | 0.29 | 0.27 |
| Discovery | 0.25 | 0.25 | 0.25 | 0.26 | 0.25 |
| MSB-105 | 0.22 | 0.21 | 0.19 | 0.22 | 0.21 |
| **MSB-1080** | **0.26** | **0.25** | **0.22** | **0.21** | **0.23** |
| MSB-109 | 0 | 0.19 | 0.24 | 0.26 | 0.25 |
| MSB-112 | 0.19 | 0 | 0.22 | 0.26 | 0.24 |
| MSB-116 | 0.24 | 0.22 | 0 | 0.19 | 0.19 |
| MSB-125 | 0.26 | 0.26 | 0.19 | 0 | 0.21 |
| MSB-154 | 0.25 | 0.24 | 0.19 | 0.21 | 0 |
| MSB-1541 | 0.25 | 0.24 | 0.2 | 0.21 | 0.22 |
| MSB-1542 | 0.25 | 0.25 | 0.26 | 0.25 | 0.24 |
| MSB-178 | 0.25 | 0.25 | 0.26 | 0.23 | 0.22 |
| MSB-278 | 0.27 | 0.26 | 0.17 | 0.21 | 0.21 |
| MSB-74 | 0.24 | 0.24 | 0.19 | 0.21 | 0.2 |
| MSB-75 | 0.26 | 0.26 | 0.19 | 0.14 | 0.21 |
| MSB-91 | 0.25 | 0.24 | 0.19 | 0.21 | 0.2 |
| MSB-97 | 0.2 | 0.2 | 0.25 | 0.28 | 0.26 |
| MSB 98 | 0.26 | 0.25 | 0.26 | 0.23 | 0.22 |
| Quickstand | 0.26 | 0.25 | 0.3 | 0.31 | 0.29 |
| Trans1 | 0.32 | 0.31 | 0.29 | 0.26 | 0.28 |
| Trans2 | 0.32 | 0.31 | 0.29 | 0.27 | 0.28 |
| U3 | 0.29 | 0.28 | 0.31 | 0.32 | 0.31 |

| Taxa | MSU1541 | MSU1542 | MSU178 | MSU278 | MSU74 |
|---|---|---|---|---|---|
| Celebration | 0.25 | 0.24 | 0.25 | 0.27 | 0.25 |
| Choice | 0.27 | 0.24 | 0.25 | 0.3 | 0.27 |
| Discovery | 0.25 | 0.24 | 0.25 | 0.27 | 0.25 |
| MSB-105 | 0.22 | 0.23 | 0.24 | 0.23 | 0.21 |
| **MSB-1080** | **0.23** | **0.23** | **0.22** | **0.23** | **0.22** |
| MSB-109 | 0.25 | 0.25 | 0.25 | 0.27 | 0.24 |
| MSB-112 | 0.24 | 0.25 | 0.25 | 0.26 | 0.24 |
| MSB-116 | 0.2 | 0.26 | 0.26 | 0.17 | 0.19 |
| MSB-125 | 0.21 | 0.25 | 0.23 | 0.21 | 0.21 |
| MSB-154 | 0.22 | 0.24 | 0.22 | 0.21 | 0.2 |
| MSB-1541 | 0 | 0.24 | 0.22 | 0.24 | 0.21 |
| MSB-1542 | 0.24 | 0 | 0.22 | 0.26 | 0.24 |
| MSB-178 | 0.22 | 0.22 | 0 | 0.27 | 0.21 |

TABLE 10-continued

Genetic distance matrix ($F_{st}$) of 'MSB-1080', 17 other lines from Mississippi State University and five commercial checks based on Single Nucleotide Polymorphism (SNP) markers.

| | | | | | |
|---|---|---|---|---|---|
| MSB-278 | 0.24 | 0.26 | 0.27 | 0 | 0.21 |
| MSB-74 | 0.21 | 0.24 | 0.21 | 0.21 | 0 |
| MSB-75 | 0.21 | 0.25 | 0.22 | 0.21 | 0.21 |
| MSB-91 | 0.21 | 0.25 | 0.21 | 0.22 | 0.15 |
| MSB-97 | 0.25 | 0.24 | 0.26 | 0.26 | 0.27 |
| MSB 98 | 0.22 | 0.21 | 0.17 | 0.26 | 0.22 |
| Quickstand | 0.29 | 0.27 | 0.28 | 0.32 | 0.3 |
| Trans1 | 0.28 | 0.25 | 0.26 | 0.17 | 0.28 |
| Trans2 | 0.28 | 0.25 | 0.26 | 0.18 | 0.28 |
| U3 | 0.3 | 0.29 | 0.3 | 0.32 | 0.3 |

| Taxa | MSU75 | MSU91 | MSU97 | MSU98 | Quickstand |
|---|---|---|---|---|---|
| Celebration | 0.26 | 0.25 | 0.25 | 0.25 | 0.28 |
| Choice | 0.29 | 0.28 | 0.19 | 0.25 | 0.22 |
| Discovery | 0.26 | 0.25 | 0.25 | 0.25 | 0.28 |
| MSB-105 | 0.23 | 0.21 | 0.23 | 0.24 | 0.26 |
| **MSB-1080** | **0.21** | **0.22** | **0.26** | **0.22** | **0.3** |
| MSB-109 | 0.26 | 0.25 | 0.2 | 0.26 | 0.26 |
| MSB-112 | 0.26 | 0.24 | 0.2 | 0.25 | 0.25 |
| MSB-116 | 0.19 | 0.19 | 0.25 | 0.26 | 0.3 |
| MSB-125 | 0.14 | 0.21 | 0.28 | 0.23 | 0.31 |
| MSB-154 | 0.21 | 0.2 | 0.26 | 0.22 | 0.29 |
| MSB-1541 | 0.21 | 0.21 | 0.25 | 0.22 | 0.29 |
| MSB-1542 | 0.25 | 0.25 | 0.24 | 0.21 | 0.27 |
| MSB-178 | 0.22 | 0.21 | 0.26 | 0.17 | 0.28 |
| MSB-278 | 0.21 | 0.22 | 0.26 | 0.26 | 0.32 |
| MSB-74 | 0.21 | 0.15 | 0.27 | 0.22 | 0.3 |
| MSB-75 | 0 | 0.21 | 0.27 | 0.23 | 0.31 |
| MSB-91 | 0.21 | 0 | 0.27 | 0.22 | 0.3 |
| MSB-97 | 0.27 | 0.27 | 0 | 0.25 | 0.25 |
| MSB 98 | 0.23 | 0.22 | 0.25 | 0 | 0.28 |
| Quickstand | 0.31 | 0.3 | 0.25 | 0.28 | 0 |
| Trans1 | 0.26 | 0.28 | 0.31 | 0.27 | 0.35 |
| Trans2 | 0.26 | 0.28 | 0.31 | 0.27 | 0.35 |
| U3 | 0.32 | 0.3 | 0.27 | 0.3 | 0.26 |

| Taxa | Trans1 | Trans2 | U3 |
|---|---|---|---|
| Celebration | 0.3 | 0.3 | 0.28 |
| Choice | 0.33 | 0.33 | 0.26 |
| Discovery | 0.3 | 0.3 | 0.29 |
| MSB-105 | 0.3 | 0.31 | 0.3 |
| **MSB-1080** | **0.26** | **0.26** | **0.3** |
| MSB-109 | 0.32 | 0.32 | 0.29 |
| MSB-112 | 0.31 | 0.31 | 0.28 |
| MSB-116 | 0.29 | 0.29 | 0.31 |
| MSB-125 | 0.26 | 0.27 | 0.32 |
| MSB-154 | 0.28 | 0.28 | 0.31 |
| MSB-1541 | 0.28 | 0.28 | 0.3 |
| MSB-1542 | 0.25 | 0.25 | 0.29 |
| MSB-178 | 0.26 | 0.26 | 0.3 |
| MSB-278 | 0.17 | 0.18 | 0.32 |
| MSB-74 | 0.28 | 0.28 | 0.3 |
| MSB-75 | 0.26 | 0.26 | 0.32 |
| MSB-91 | 0.28 | 0.28 | 0.3 |
| MSB-97 | 0.31 | 0.31 | 0.27 |
| MSB 98 | 0.27 | 0.27 | 0.3 |
| Quickstand | 0.35 | 0.35 | 0.26 |
| Trans1 | 0 | 0.03 | 0.32 |
| Trans2 | 0.03 | 0 | 0.32 |
| U3 | 0.32 | 0.32 | 0 |

I claim:

1. A new and distinct variety of Bermudagrass plant named 'MSB-1080' as shown and described herein.

* * * * *